(12) United States Patent
Lindenmeier et al.

(10) Patent No.: US 6,565,558 B1
(45) Date of Patent: May 20, 2003

(54) HIGH-FREQUENCY DEVICE FOR GENERATING A PLASMA ARC FOR THE TREATMENT OF BIOLOGICAL TISSUE

(76) Inventors: Heinz Lindenmeier, Forstenriederstrasse 7, Planegg (DE), D-82152; Karl Fastenmeier, Pasettiweg 2, München (DE), D-81739

( * ) Notice: Subject to any disclaimer, the term of this patent is extended or adjusted under 35 U.S.C. 154(b) by 0 days.

(21) Appl. No.: 09/763,937
(22) PCT Filed: Sep. 1, 1999
(86) PCT No.: PCT/EP99/06437
§ 371 (c)(1),
(2), (4) Date: Feb. 27, 2001
(87) PCT Pub. No.: WO00/12019
PCT Pub. Date: Mar. 9, 2000

(30) Foreign Application Priority Data

Sep. 1, 1998 (DE) .......................... 198 39 826

(51) Int. Cl.$^7$ ............................ A61B 17/36; A61B 17/20
(52) U.S. Cl. ............................ 606/34; 607/49; 607/41; 607/40; 607/105; 606/96; 606/99; 604/22
(58) Field of Search .................. 606/34, 35–45, 606/49; 604/114, 22, 113, 23; 607/99, 105–110

(56) References Cited

U.S. PATENT DOCUMENTS 3,903,891 A 9/1975 Brayshaw
4,781,175 A * 11/1988 McGreevy et al. ..... 128/303.13
6,099,523 A * 8/2000 Kim et al. ..................... 606/40
6,149,620 A * 11/2000 Baker et al. .................. 604/22
6,296,636 B1 * 10/2001 Cheng et al. .................. 606/32

FOREIGN PATENT DOCUMENTS

WO          WO 98/35618          8/1998

\* cited by examiner

*Primary Examiner*—Mark Paschall
(74) *Attorney, Agent, or Firm*—Merchant & Gould P.C.

(57) ABSTRACT

High-frequency device to generate a plasma arc (5) for the treatment of biological tissue (1), in particular in medicine, with a high-frequency generator (3) having an internal resistor (8) and, connected thereto by means of a flexible lead (10), an electrode (4) with which the plasma arc (5) is produced in a plasma segment (6) between the electrode (4) and the biological tissue (1), which is likewise electrically connected to the high-frequency generator (3), such that in the high-frequency generator (3) a high-frequency voltage source (7) is provided to which is connected a resonant circuit (2) that comprises a first reactance element (9*a*) with a capacitive action and, in series therewith, a second reactance element (9*a*) with an inductive action, and that has a resonant frequency at the frequency of the high-frequency oscillation emitted by the high-frequency voltage source (7), wherein the voltage to generate the plasma arc (5) is derived from the first or second reactance element (9*a*, 9*b*).

25 Claims, 12 Drawing Sheets

Figure 1:
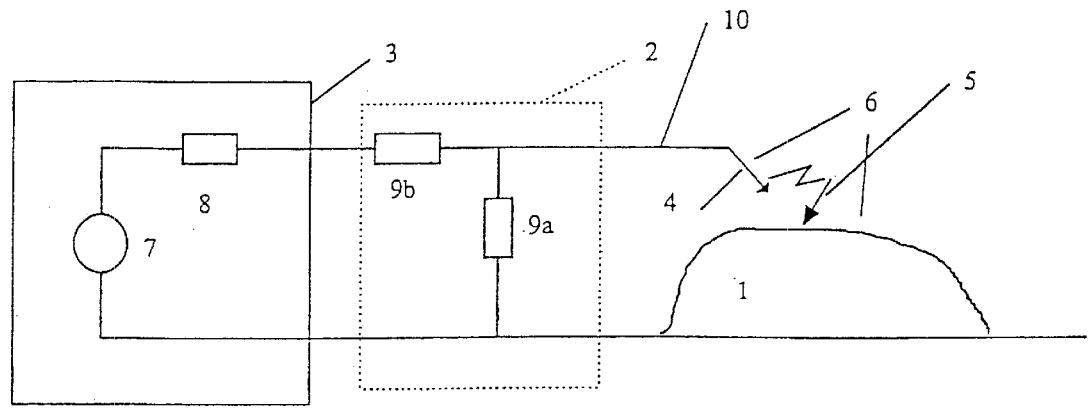

HIGH-FREQUENCY DEVICE FOR GENERATING A PLASMA ARC FOR THE TREATMENT OF BIOLOGICAL TISSUE

DESCRIPTION

The invention relates to a high-frequency device to generate a plasma arc for the treatment of biological tissue according to the precharacterizing clause of claim 1.

High-frequency devices of this kind have been disclosed in the patents DE-OS 37 10 489, EP 0 353 178 A2 and WO 93/01758. The surfaces of human tissues can be treated in a medium consisting of varous gases. Often the spatial configuration of the plasma beam can be improved by directing towards the tissue a concentrated beam of a gas, the ionization field strength of which is lower than that of the gas in the surrounding area.

Regarding the supply of the high-frequency energy that is needed to generate a plasma beam, in all cases there are two fundamentally problematic considerations. First, it is necessary to ignite the plasma beam reliably after it has become extinguished during use and when it is initially turned on. Second, the HF current intensity in the ignited plasma beam should be adjustable so that the intensity is suitable for the particular medical application.

The latter problem is extensively evaluated in DE-OS 37 10 489 and in EP 0 353 178 A2, and is solved by an extremely complicated device for the regulation and control of the energy supplied to the plasma. The controlled system here consists of a HF driver circuit that charges an output oscillator with a predetermined frequency, such that the output oscillator discharges at its resonant frequency so as to deliver electrical energy to the tissue. By means of frequency dividers, frequency signals are obtained with which to control the application and the duration of the feeder or driver pulses sent to the output oscillator. The HF driver circuit thus has a switching function within a complicated control circuit. In order for such a device to produce reliable ignition with an electrode voltage substantially above the ignition voltage of the plasma beam, it is essential to adjust the driver pulses so that they last for a relatively long time. After ignition of the plasma by the control system, the intensity must be adjusted to a level suitable for the medical application in a short time, which is predetermined by the time constant of the control system.

The objective of the invention is therefore to improve the high-frequency device to generate a plasma arc according to the precharacterizing clause of claim 1 by means of a simple circuit.

This objective is achieved by a high-frequency device with the characteristics of claim 1.

With the present circuit, when the plasma is in the non-ignited state, the high-frequency voltage at the electrode is appreciably above the level needed to ignite the plasma arc, and when the plasma is in the ignited state, the high-frequency current within the plasma has the intensity suitable for the specific medical application; similarly, if the plasma arc becomes extinguished during use, the high-frequency voltage at the electrode again rises to a level above that needed to ignite the plasma arc, so that re-ignition occurs automatically.

A substantial advantage of the solution in accordance with the invention is that without the provision of additional control circuitry, and hence with no elaborate technical additions, a stable and precisely controllable plasma segment can be maintained between the electrode and the point at which the plasma arc is intended to enter the tissue. As a result, the method becomes suitable for additional applications (e.g., in the area of neurosurgery and for lesions of the oesophageal mucosa) for which HF surgery could not previously be used because of the great risk of thermal damage to adjacent parts of the tissue.

Another substantial advantage lies in the fact that with the proposed solution the high-frequency energy is essentially all converted to heat at or within the tissue, because no effective resistances are required for control. This eliminates the need for large cooling surfaces or for active cooling by means of ventilators (which is extremely undesirable in the clinical context), and provides considerable savings with respect to the complexity and size of the device as well as the energy expenditure during use. The device thus becomes more acceptable for clinical applications.

Figure 2A:
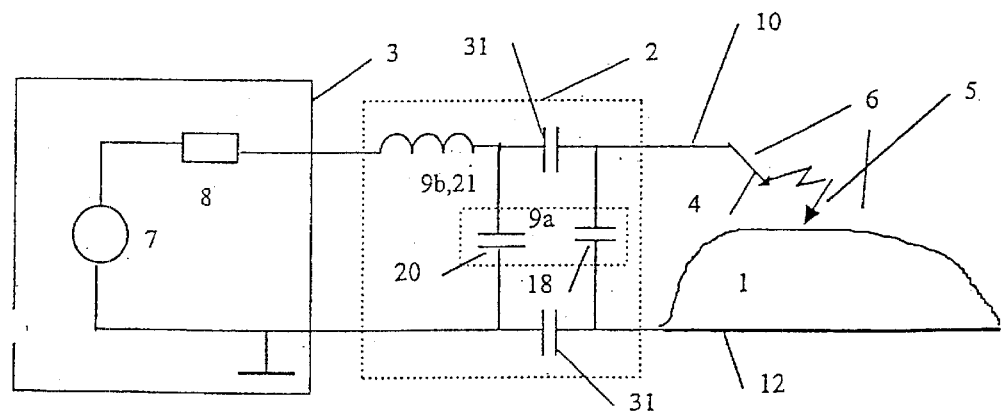
Figure 2B:
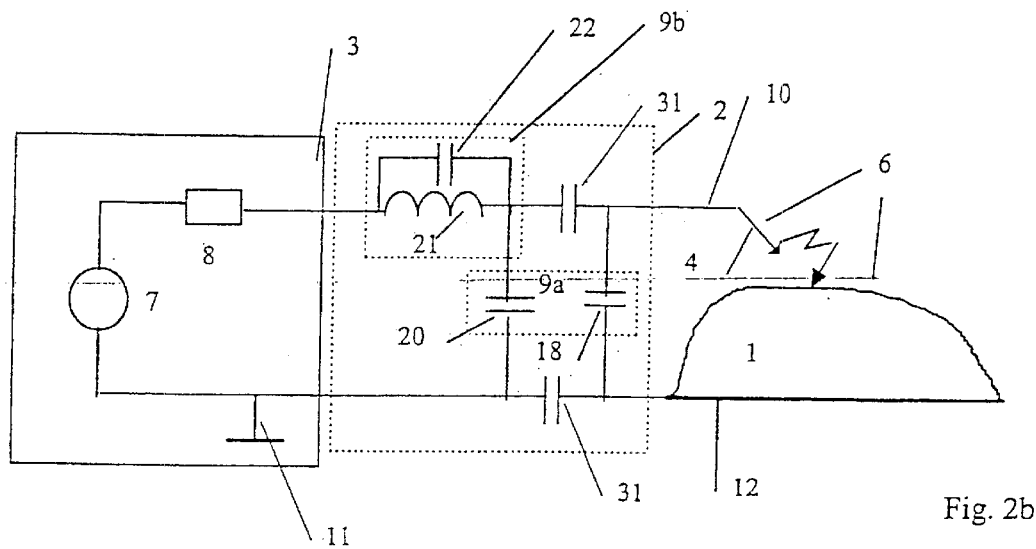
Figure 2C:
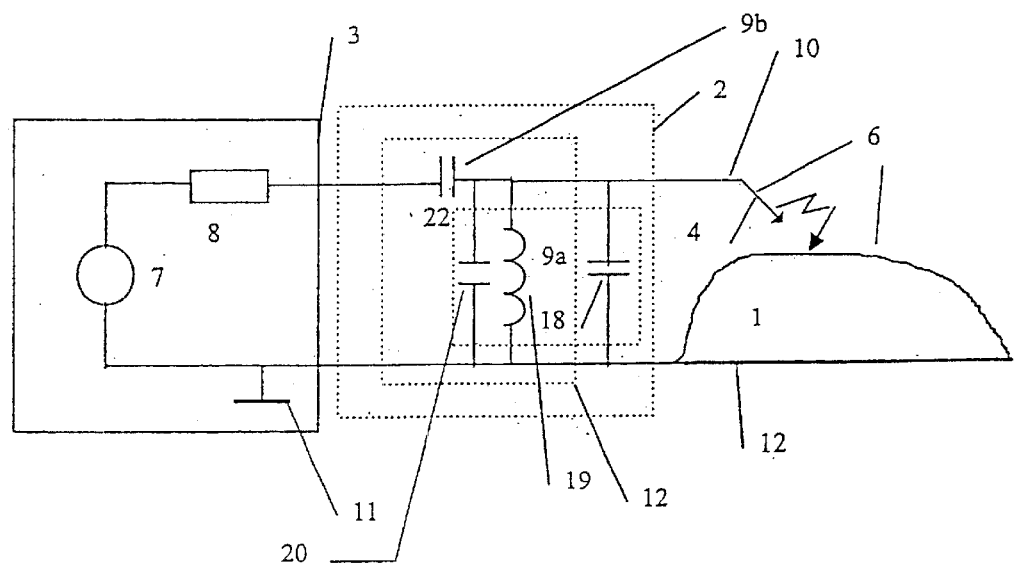
Figure 3:
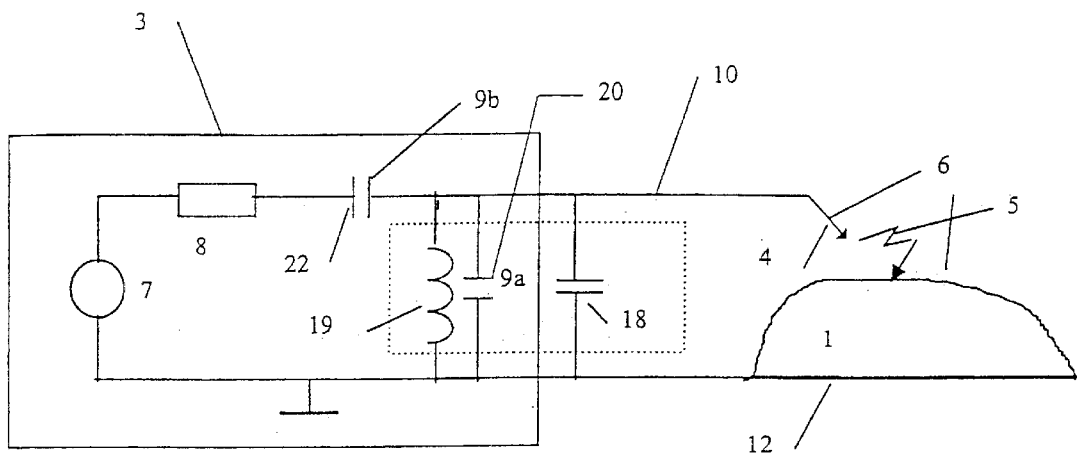
Figure 4A:
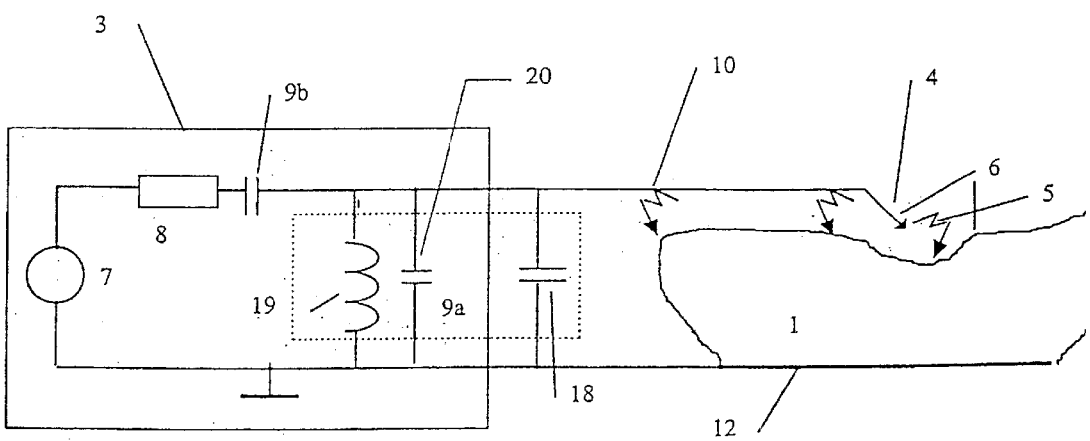
Figure 4B:
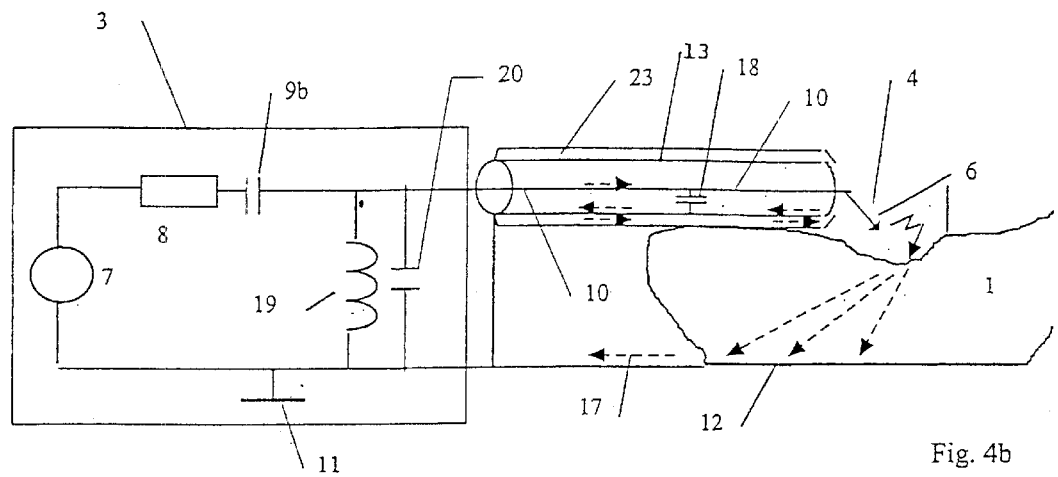
Figure 4C:
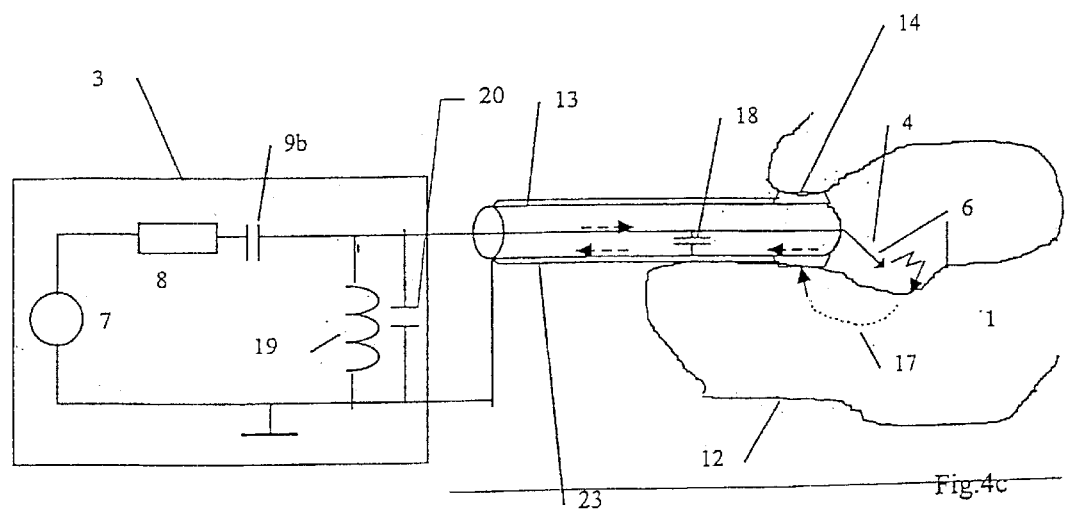
Figure 4D:
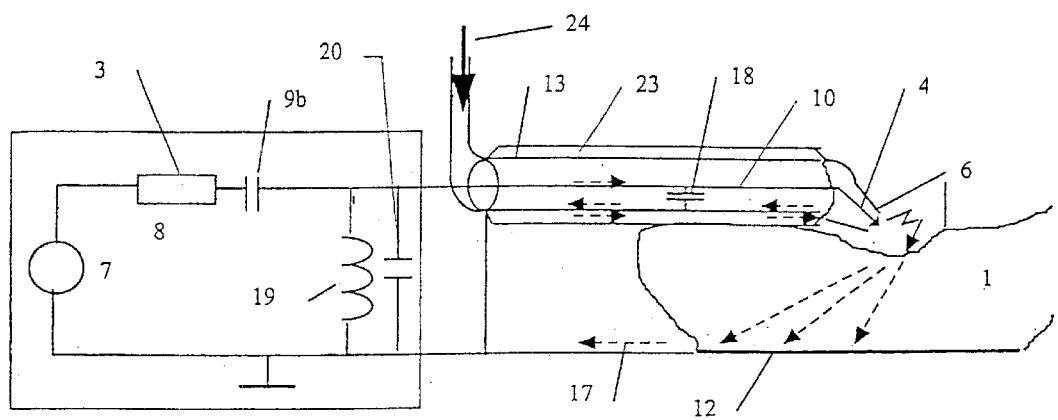
Figure 4E:
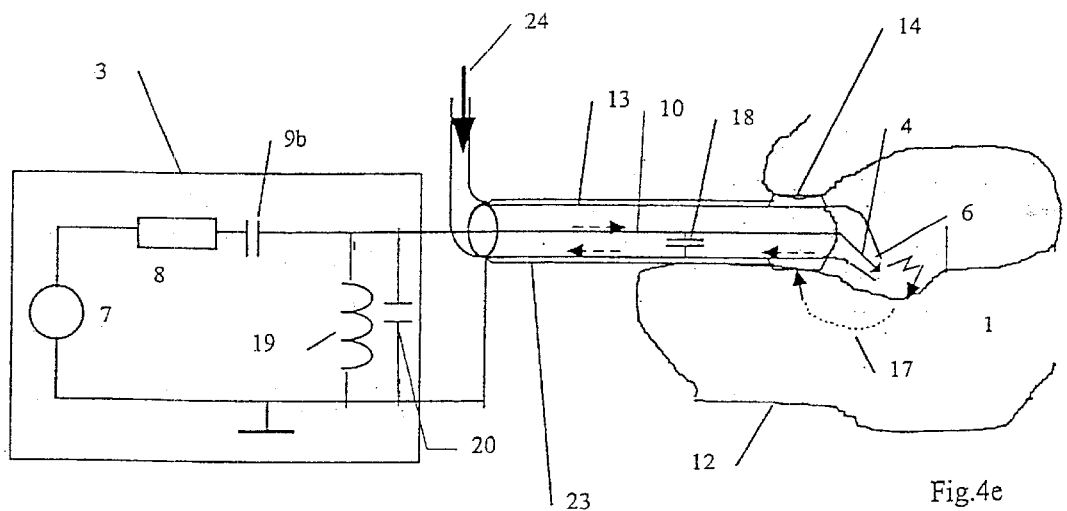
Figure 4F:
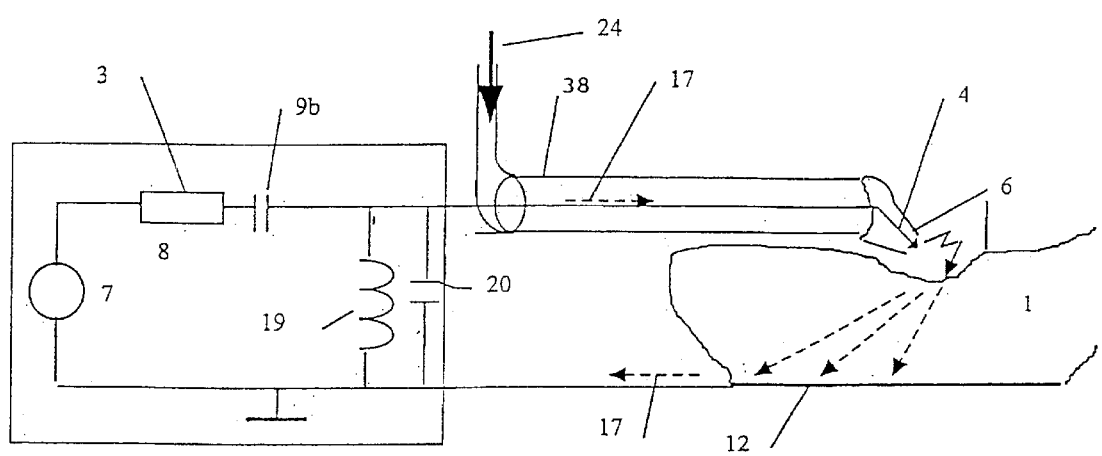
Figure 5A:
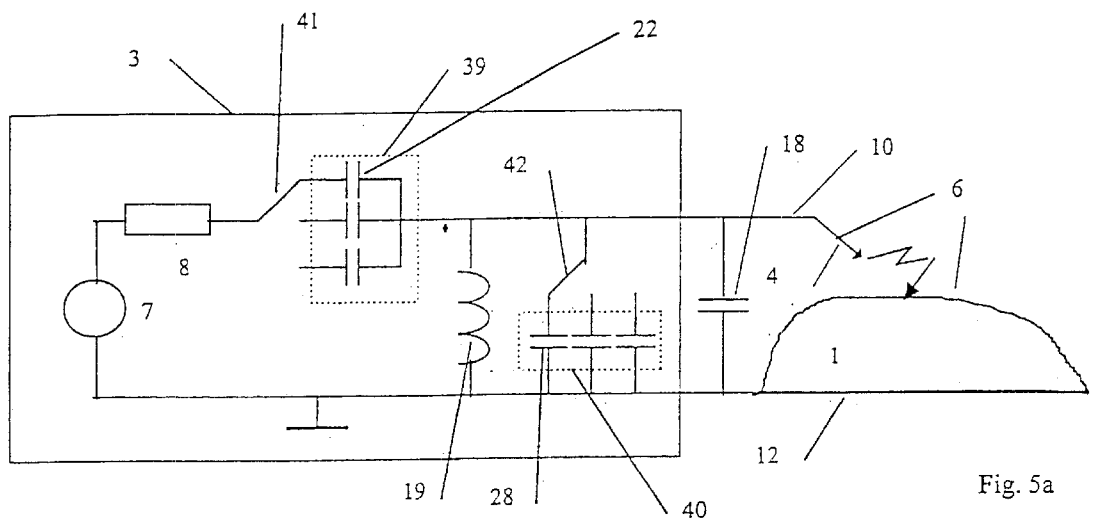
Figure 5B:
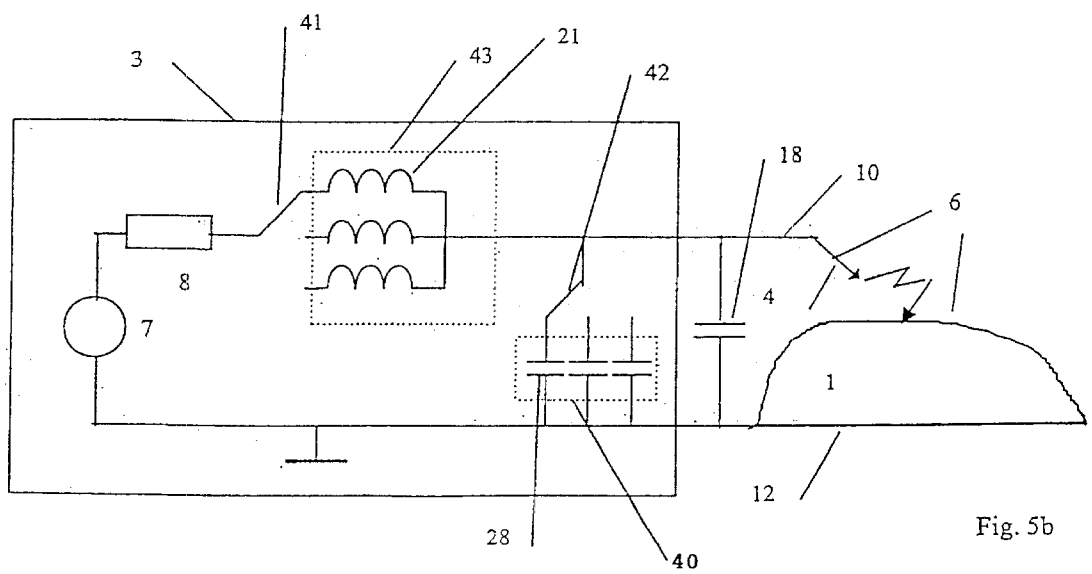
Figure 6A:
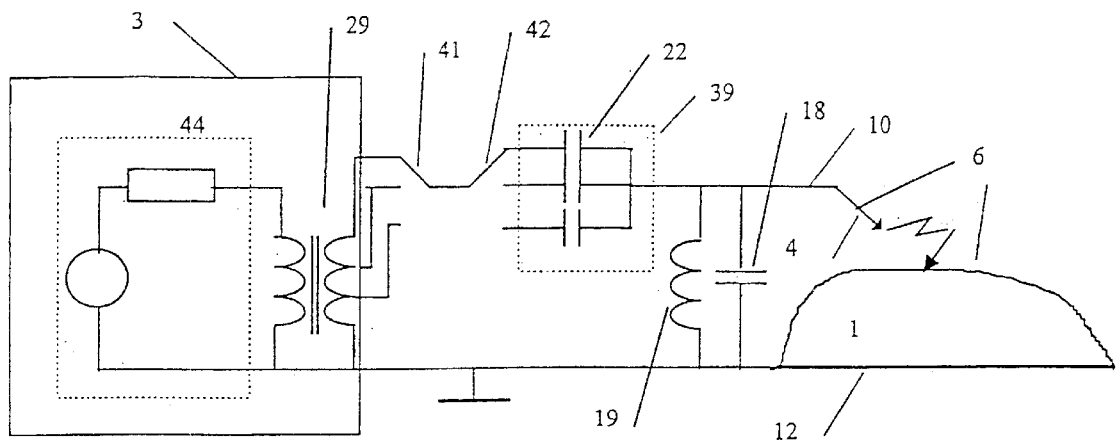
Figure 6B:
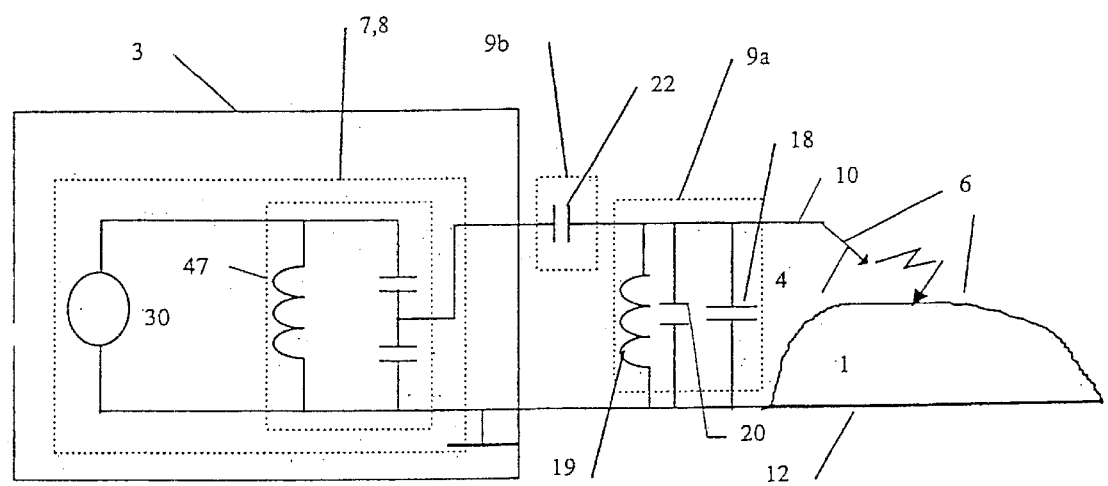
Figure 7:
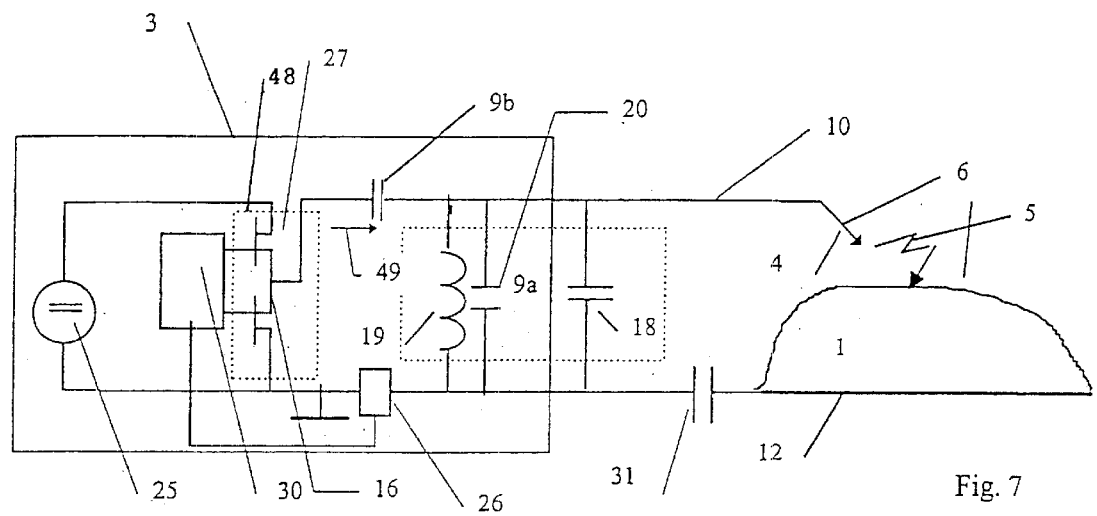
Figure 8:
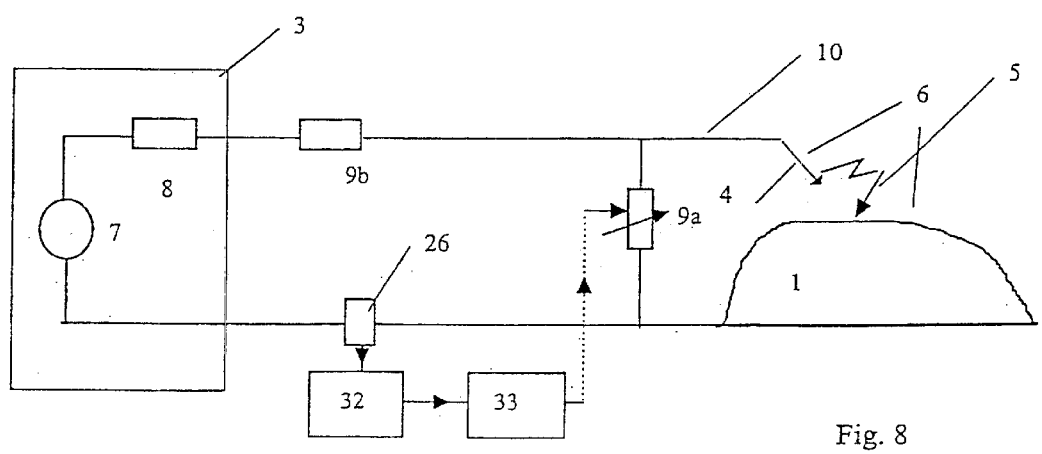
Figure 9:
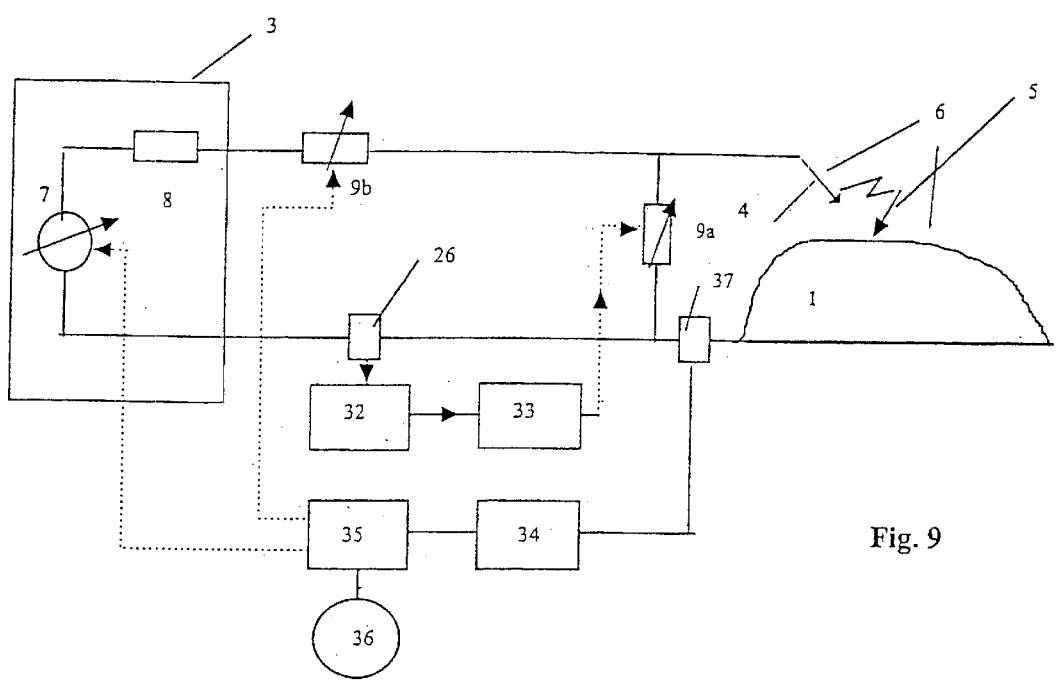
Figure 10:
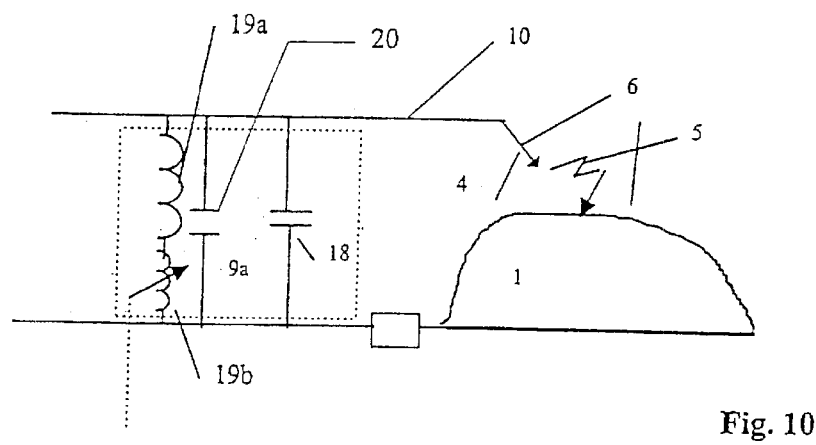
Figure 11:
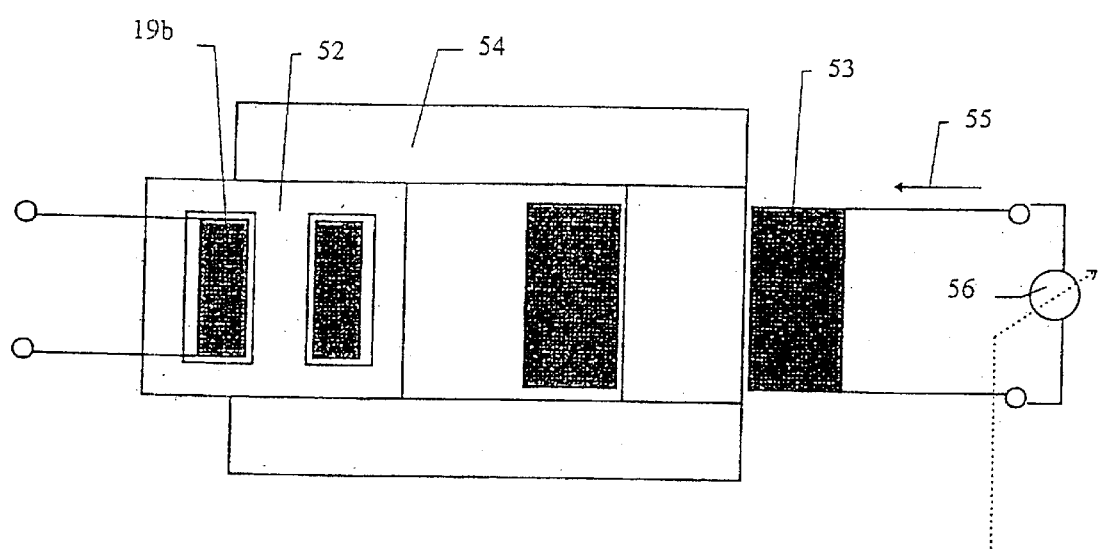

Exemplary embodiments of the invention shown in the drawings are described in detail below. The individual figures are as follows:

FIG. 1 shows a high-frequency device to generate a plasma arc according to one embodiment of the invention, FIG. 2a shows a high-frequency device according to FIG. 1 with a reactance element 9a consisting of a capacitor and the capacitance of the electrode lead, and a reactance element 9b comprising an inductor, FIG. 2b shows a high-frequency device according to FIG. 1 with a series inductive reactance element 9b, FIG. 2c shows a high-frequency device according to FIG. 1 with a reactance element 9a formed by the parallel wiring of a parallel inductance with parallel capacitance and the electrode-lead capacitance, and a series capacitor as the second reactance element 9b, FIG. 3 shows a high-frequency device according to FIG. 2c with a series capacitor disposed in the housing of the high-frequency generator as the second reactance element 9b, FIG. 4a shows a high-frequency device according to FIG. 3 with an insulated lead to the operation site, designed to be unipolar with respect to the patient and to the electrode;

FIG. 4b shows a high-frequency device according to FIG. 3 with a lead to the electrode that comprises a coaxial shielded cable earthed in a manner suitable for high frequencies, with insulation layer, FIG. 4c shows a high-frequency device according to FIG. 3 with a lead that at its distal end has a built-in earth electrode that connects the coaxial shielded cable electrically to the human tissue, FIG. 4d shows a high-frequency device according to FIG. 3 with a lead according to FIG. 4b and with a stream of noble gas that is conducted through the interior of the coaxial shielded cable to the electrode and the operation site in the human tissue, FIG. 4e shows a high-frequency device according to FIG. 3 with a lead according to FIG. 4c and with a stream of noble gas that is conducted through the interior of the coaxial shielded cable to the electrode and the operation site in the human tissue, FIG. 4f shows a high-frequency device according to FIG. 3 with a lead according to FIG. 4a but with an insulating tube that surrounds the lead, through the interior of which the noble gas flows to the electrode and to the operation site in the human tissue, FIG. 5a shows a high-frequency device according to FIG. 3 with a first capacitor battery and a second capacitor battery, FIG. 5b shows a high-frequency device according to FIG. 2a, but with a capacitor battery and a battery of inductors, FIG. 6a shows a high-frequency device with a transformer that has a selectable voltage ratio, FIG. 6b shows a high-frequency device with a high-frequency generator having low internal resistance, which is formed by a high-resistance HF current source with resonance transformation, FIG. 7 shows a high-frequency device according to FIG. 3 in which the high-frequency voltage source with internal resistance is formed by a complementary transistor stage with switching transistors, which acts as a switch, FIG. 8 shows a high-frequency device according to FIG. 1 with a generator set to a specified frequency and a resonant circuit, FIG. 9 shows a high-frequency device according to FIG. 8 in which the plasma current can be adjusted to the level needed for the medical application by means of a patient-current decoupler, a patient-current indicator and a downstream patient-current regulator, FIG. 10 shows a high-frequency device according to FIG. 8 or FIG. 9 with an adjustable first reactance element 9a, FIG. 11 shows, as an example, a variable inductor for the inertia-free tuning of the resonance for arrangements according to FIGS. 8 to 10, FIG. 12 shows an example of an arrangement with tuning and adjustment of the intensity of the plasma current.

The operation of the present invention is first described with reference to the arrangement in FIG. 1.

This arrangement comprises a high-frequency generator 3, which consists of a high-frequency voltage source 7 with an internal resistor 8. Connected to this high-frequency generator 3, which emits periodic high-frequency oscillations, is a series circuit consisting of a second reactance element 9b and a first reactance element 9a. The (increased) resonance voltage produced at the first reactance element 9a is in proportion to the unavoidable losses in the two reactance elements in combination with the damping resistance introduced by the internal resistor 8. Whenever the amplitude of this voltage is larger than required for the ignition of a plasma arc 5 between an electrode 4 and the human tissue 1, the plasma arc 5 will develop immediately.

The arc drop voltage of the plasma segment 6 is known to be below the ignition voltage. Because of the damping of the resonance arrangement brought about by the plasma current, after ignition a plasma current is established, the intensity of which depends very substantially on the voltage of the high-frequency voltage source 7, the value of the second reactance element 9b and the damping of the first reactance element 9a and the second reactance element 9b.

Hence it is advantageous to make the internal resistance 8 small at the resonant frequency, in comparison to the reactances of the first reactance element 9a and the second reactance element 9b.

For the special case of a negligibly small, low-impedance internal resistor 8 and of an attenuation loss in the first reactance element 9a and the second reactance element 9b that is negligible in comparison to the damping by the plasma current, as well as for the case that the arc drop voltage of the plasma arc 5 is substantially below the ignition voltage, the plasma current is determined mainly by the magnitude of the second reactance 9b, when the voltage of the high-frequency voltage source 7 is substantially larger than the arc drop voltage of the plasma arc 5.

The considerable advantage associated with the invention is the immediate re-ignition of the plasma arc when it has become extinguished owing to manipulation during an operation. The reason is that when the plasma current becomes extinguished and hence the damping of the resonance arrangement it causes is eliminated, the voltage rises at the first reactance element 9a and thus at the plasma segment 6 until it has returned to the level that is present during weak damping of the resonance, as a result of which the plasma segment is independently reignited. Therefore no control device is required for this purpose.

The time needed for re-ignition after the arc is extinguished is of the order of magnitude of a few cycles of the high-frequency oscillation, which if the overall damping is small is extremely short in comparison to the time perceptible by the operator.

Another advantage of the invention lies in the fact that the high-frequency generator is not required to emit a sinusoidal voltage. The voltage must merely be periodic and contain an appreciable spectral component at the resonant frequency of the resonant circuit 2. Nevertheless, the resonant circuit 2 causes the current in the resonance loop, and hence the patient current, to be largely sinusoidal, to the extent allowed by the selectivity.

In FIGS. 2a to 2c examples are shown of various advantageous implementations of the high-frequency generator 3 with downstream resonant circuit 2.

In FIG. 2a the first reactance element 9a takes the form of a shunt capacitor 20 disposed in parallel with the effective capacitance 18, which exists between the lead to the electrode 4 and the surroundings, specifically the human tissue 1. As second reactance element 9b an inductor 21 is used, which with a real internal resistor 8 fulfills the resonance condition. In the case of an internal resistance 8 provided with a reactive component, the resonant circuit 2 together with this internal resistance 8 fulfills the resonance condition at a slightly different frequency, which does not alter the essence of the arrangement.

For reasons of safety an earth connection is provided in the high-frequency generator 3. Safety regulations further demand that the patient be electrically separated from the housing earth connection. Therefore in FIG. 2a capacitors 31 for protection against electric shock are shown, but their capacitance is made so large that they do not affect the high-frequency behaviour. Therefore they are not shown everywhere in the following figures.

In the arrangement shown in FIG. 2b, in parallel to the series inductor 21 there is a series capacitor 22, which can act as internal capacitance of the series inductor 21 or is inserted for the purpose of fine-tuning.

In an advantageous embodiment of the invention, as shown in FIG. 2c, an inductor 19 is inserted parallel to the shunt capacitor 20, which is often unavoidable or is used for tuning, in order to form the first reactance element 9a, which as a whole has an inductive action. This is associated with the advantage that the inductor is situated in the parallel branch and thus can be connected on one side to the earth connection. The second reactance element 9b then takes the form of a capacitor. There is a connection between the human tissue 1 and the earth connection 11 of the high-frequency generator 3, which is at earth potential.

In another advantageous embodiment of the invention, shown in FIG. 3, the essential elements of the resonant circuit 2 are disposed within the housing of the high-frequency generator 3. These elements include an inductor 19 in parallel with the plasma segment 6. The only part of the first reactance element 9a that is disposed outside the high-frequency generator 3 is the effective capacitance 18, i.e. the capacitance of the lead 10 to the plasma segment 6.

FIG. 4a illustrates the problem that when the electrode lead 10 is not insulated, the plasma can be ignited and conduct to the tissue at undesired places, outside the plasma arc 5. This situation is indicated by arrows in FIG. 4a. In an advantageous embodiment of the invention, therefore, the electrode lead 10 is surrounded by a coaxial shielding conductor 13, which is covered with an insulation layer 23. This is shown in FIG. 4b. Here the dashed arrows describe the forward and return currents 17 that develop in this arrangement during use. The coaxial shielding conductor 13 prevents the development of plasma arcs between the lead 10 and the human tissue 1. The plasma current flows as a tissue current within the human tissue 1 to the external HF-earth electrode 12 in contact with the patient, and is conducted back to the high-frequency generator 3. On the outer skin of the shielding conductor flow currents that do not affect the operation. In this way it is ensured that the plasma arc 5 is formed exclusively between the electrode 4 and the human tissue 1.

In some kinds of operation damage can be caused if the return current of the plasma arc 5 flows along an uncontrolled, diffuse path through the human tissue 1 to the external HF earth electrode 12. In such cases, with respect to the spatial selectivity of the formation of the plasma arc 5 in connection with a locally restricted conduction of the return current in the human tissue 1 to the coaxial shielding conductor 13, it is advantageous for the coaxial shielding conductor 13 to be provided at its distal end with a built-in HF earth electrode 14, which there is in conductive contact with the human tissue 1. A corresponding arrangement is shown in FIG. 4c. The return current 17 is locally restricted to the immediate surroundings of the operation site, and flows back along the inside of the coaxial shielding conductor 13.

A further advantageous application of the invention is evident in combination with the provision a stream of noble gas 24 that is directed onto the operation site. The conduit for the gas can advantageously consist of a cavity within the coaxial shielding conductor 13, as shown in FIG. 4d. By applying the noble-gas stream 24, the ionization energy is greatly reduced, as a result of which the ignition voltage for the plasma segment 6 is also substantially lowered and no ionization occurs outside the stream of noble gas. A suitable noble gas, for example, is argon, which finds many applications. The noble-gas stream 24, which is applied in such a way that at the distal end it is suitably positioned for supporting the development of the plasma arc 5, permits high selectivity with respect to the spatial extent of the plasma arc 5.

For the same reason, in an arrangement like that in FIG. 4c a noble-gas stream 24 is carried within the shielding conductor 13, as shown in FIG. 4e. Alternatively, the noble-gas stream can also be passed through a hollow internal lead.

In contrast, in the arrangement shown in FIG. 4f with a unipolar lead to the electrode, no coaxial shielding conductor 13 is used but rather, in its place, an insulating tube 38 within which the noble-gas stream 24 passes to the electrode 4.

In the preferred embodiment shown in FIG. 5a the capacitor battery 39 consists, for example, of 50-pF, 100-pF and 200-pF capacitors whereas the capacitances in the battery 40 are 16 pF, 116 pF and 216 pF; the capacitor 18 has a capacitance of 250 pF and the inductor 19 has a value of ca. 500 $\mu$H; and the high-frequency generator is operated at a frequency of 330 kHz. The voltage generated by the high-frequency voltage source 7 is regulated within the range between 40 and 300 V, and the operation can be carried out with the electrode 4 at a distance of 1 to about 25 mm from the human tissue 1.

In FIG. 5a and 5b various means of adjusting the resonance conditions and the intensity of the plasma current during the operation are shown. In one particularly advantageous arrangement, shown in FIG. 5a, a first capacitor battery 39 and a second capacitor battery 40 are provided, from each of which a suitable capacitance can be selected by means of a switch: the first switch 41 in the case of the series capacitor 22, and the second switch 42 for the capacitor 28. By combining the switch positions and hence the capacitances suitably, for a given inductance value of the parallel inductor 19 both the resonance conditions for the frequency of the high-frequency voltage source 7 and the intensity of the plasma arc 5 at the given voltage of the high-frequency voltage source 7 are adjusted.

As another possibility, in FIG. 5b the second reactance element 9b takes the form of a series inductor 21, in which case the first switch 41 selects the desired inductance from an inductor battery 43. The first reactance element 9a is chosen by selecting a suitable capacitor 28 in a capacitor battery 40 by means of a second switch 42.

In many cases the high-frequency generator 44 provided for constructing a high-frequency device to produce a plasma arc is designed so that it can also be used for other applications. In this case it is advantageous to use the arrangement shown in FIG. 6a, in which a transformer 29 that enables one of several voltage ratios to be selected is provided, and the voltage ratio is selected by means of a first switch 41. A second switch 42 is then used to select a series capacitor 22 from a first capacitor battery 39. If the only high-frequency voltage source available is a high-impedance HF-current source 15, it can be converted to a high-frequency voltage source 7 with low-impedance internal resistor 8. This is done as shown in FIG. 6b, by means of a resonance transformation circuit 47. The high-frequency generator identified by the numeral 3 in this figure then forms at its output the high-frequency voltage source 7 with low-impedance internal resistor 8.

The shape of the signal used in the present invention fulfills only the prerequisite of periodicity. It has been mentioned as a special advantage of the invention that when the plasma arc becomes extinguished, because this event eliminates the damping of the resonant circuit that is otherwise present, the voltage drop between the electrode 4 and the human tissue 1 increases so as to exceed the ignition voltage in the shortest possible time. For this advantage to be achieved, no control device (e.g., to regulate the current conduction angle) is needed.

In the embodiment shown in FIG. 7 the high-frequency generator 3 is composed of a DC voltage source 25 and a complementary circuit 48 comprising switching transistors 27. The switching transistors 27 have a push-pull action and are triggered by a pulse generator 30. The two transistors are alternately fully conducting and fully blocked and operate in pure switching mode. As a result, at their common source electrode 16 a rectangular voltage waveform is produced, with a mean value equal to half the voltage of the DC voltage source 25. This rectangular waveform is sent directly to the resonant circuit 2, which consists of the first reactance element 9a and second reactance element 9b.

By means of the current decoupler 26 pulses in the pulse generator 30 are diverted to trigger the switching transistors 27 synchronously, so that the whole arrangement can be configured as a free-running oscillator. Because of the frequency-selective action of the resonant circuit 2, the series resonant circuit permits only sinusoidal currents at the fundamental frequency of the rectangular voltage waveform. When the overall circuitry is correctly adjusted, each of the switching transistors 27 is switched at the time when the resonant-circuit current 49 passes through zero. This is a particularly low-loss arrangement, because the transistors operate in pure switching mode and each transistor conducts current only when the voltage applied to it has been reduced to the residual voltage.

When a high-frequency generator 3 with predetermined intrinsic frequency is used, the resonant circuit 2, consisting of first reactance element 9a and second reactance element 9b, must have its resonant frequency tuned to match the frequency of the high-frequency generator 3. This can be done as shown in FIG. 8, by regulating the first reactance element 9a automatically; for this purpose, the current in the resonant circuit is measured by means of an amplitude indicator 32 connected to the current decoupler 26, and a regulator 33 is used to regulate the intensity of the resonant-circuit current 49 to a maximum.

FIG. 9 shows, in an advantageous embodiment of the invention, the way in which the intensity of the current in the plasma arc 5 can also be regulated. This is done by means of a patient-current decoupler 37 and a patient-current indicator 34 in combination with a patient-current regulator 35, which is simultaneously provided with a set-point value by a patient-current set-point transmitter 36. By adjusting the second reactance element 9b and the output voltage of the high-frequency voltage source 7, the plasma current is set to the desired level, namely the value prescribed by the set-point transmitter 36.

It is also possible to adjust the current in the plasma arc 5 to the desired intensity in an especially simple manner as shown in FIGS. 5a and 6a, by choosing a fixed capacitor as the second reactance element 9b, and the regulation can be made inertia-free by adjusting the output voltage of the high-frequency voltage source 7. The inertia-free regulation of the high-frequency voltage source can be carried out, e.g. in the arrangement according to FIG. 7, by regulating the voltage of DC voltage source 25 without inertia in a manner known per se, so that the high-frequency rectangular voltage waveform at the source electrodes 16 is regulated and, consequently, the intensity of the current in plasma arc 5 is also regulated with no inertia.

In this situation is proves particularly advantageous for the adjustment of the resonant frequency of the resonant circuit 2 to the frequency of the high-frequency generator 3 also to be made inertia-free. This can advantageously be accomplished, for example, by regulating the first reactance element 9a as shown in FIG. 10; here, for the purpose of tuning, the element 9a is subdivided into an invariable inductor component 19a and a variable inductor 19b. This variable inductor 19b for the inertia-free tuning of the resonance can likewise be used for arrangements according to FIGS. 8 and 9. The variation of the inductor 19b can, as shown in FIG. 11, be accomplished for instance by premagnetization of a ferrite core with variable permeability 52. The premagnetization is altered by flow of premagnetization current 55 through the premagnetization winding 53 with the help of the premagnetization yoke 54. The variable premagnetization current 55 is adjusted by means of the variable DC voltage source 56, which is constructed in a manner known per se and is controlled by the regulator 33. An element configured in this way to serve as a first reactance element 9a or, where appropriate, also a second reactance element 9b has the advantage that it stores a high level of energy without causing distortions of the high-frequency oscillation.

Figure 12:
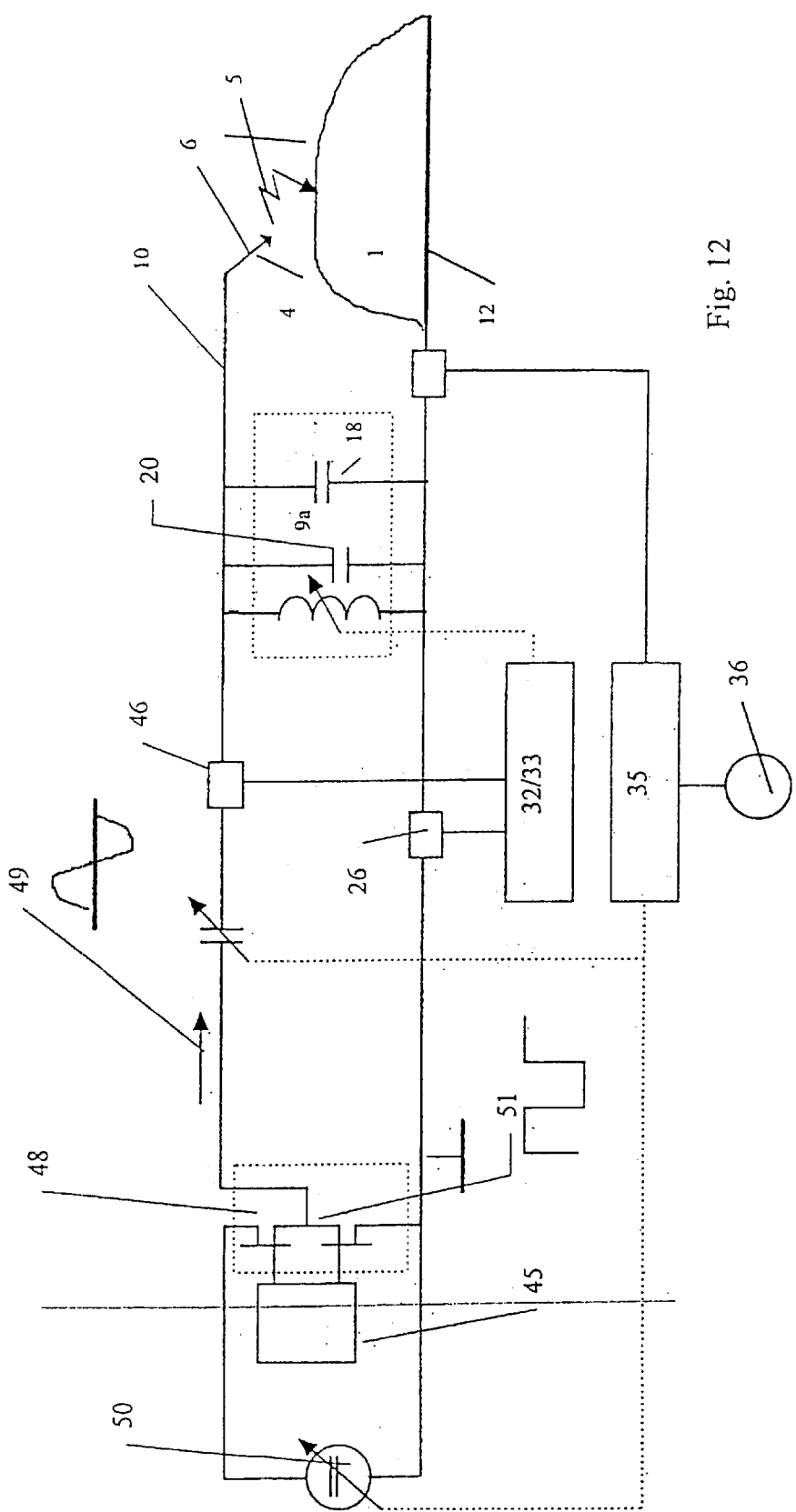

In FIG. 12 an arrangement is shown in which the plasma current is tuned and adjusted in intensity as explained with reference to FIG. 9. The high-frequency generator comprises switching transistors 27 and thus resembles that shown in FIG. 7. However, in this example the switching transistors 27 are advantageously triggered with a self-starting oscillator 45. Thus problems in stimulating the oscillations of the high-frequency generator 3 can be avoided. The intensity of the plasma current can be controlled by varying the voltage of a regulatable mains supply unit 50, by switching between capacitors in the second reactance element 9b or by both these measures. An inertia-free regulation of the resonance is advantageously achieved by varying the inductance in the first reactance element 9a, by premagnetization of the magnetic core of the inductor.

LIST OF REFERENCE NUMERALS

1 Human tissue
2 Resonant circuit
3 High-frequency generator
4 Electrode
5 Plasma arc
6 Plasma segment
7 High-frequency voltage source
8 Internal resistance
9a First reactance element
9b Second reactance element
10 Lead to electrode
11 Earth connection
12 External HF earth electrode
13 Coaxial shielded lead
14 Built-in HF earth electrode
15 High-impedance HF current source
16 Source electrodes
17 Forward and return currents
18 Effective capacitance
19 Parallel inductor
19a Inductor component
19b Variable inductor
20 Parallel capacitor
21 Series inductor
22 Series capacitor
23 Insulation layer
24 Noble-gas stream
25 DC voltage source
26 Current decoupler
27 Switching transistors
28 Suitable capacitor
29 Transformer
30 Pulse generator
31 Capacitor for protection against electric shock
32 Amplitude indicator
33 Regulator
34 Patient-current indicator
35 Patient-current regulator
36 Patient-current set-point transmitter
37 Patient-current decoupler
38 Insulating tube
39 First capacitor battery
40 Second capacitor battery
41 First switch
42 Second switch
43 Battery of inductors
44 Preset HF generator 45 Self-starting oscillator
46 Voltage decoupler
47 Resonant transformation circuit
48 Switched transistor end stage
49 Resonant-circuit current
50 Regulatable mains supply unit
51 Square-wave HF voltage
52 Ferrite core with variable permeability
53 Premagnetization winding
54 Premagnetization yoke
55 Premagnetization current
56 Variable DC voltage source

What is claimed is:

1. High-frequency device to generate a plasma arc for the treatment or biological tissue with a high-frequency generator having an internal resistor and, connected thereto by means of a flexible lead, an electrode with which the plasma arc is produced in a plasma segment between the electrode and the biological tissue, which is likewise electrically connected to the high-frequency generator, wherein the high-frequency generator comprises a high-frequency voltage source connected a resonant circuit that comprises a first reactance element with a capacitive action and, in series therewith, a second reactance element with an inductive action, and that has a resonant frequency permanently set to the frequency of the high-frequency oscillation emitted by the high-frequency voltage source, wherein the voltage to generate the plasma arc is derived from the first or second reactance element and the internal resistance of the high-frequency voltage source is substantially smaller than the reactance of the first reactance element and of the second reactance element at the resonant frequency of the resonant circuit.

2. High-frequency device to generate a plasma according to claim 1 wherein the first and second reactances have a substantially identical magnitude at the resonant frequency and the plasma segment is at least in parts disposed in parallel with a first one of the two reactance elements, wherein the magnitude of the reactances is matched to the voltage amplitude of the high-frequency voltage source in such a way that, on one hand, in a state such that the plasma arc is extinguished the high-frequency voltage at the plasma segment as a result of the resonance is at least equal to the voltage needed to ignite the plasma arc and, on the other hand, in a state such that the plasma arc exists the resonance is damped by the conductance of the plasma segment and the magnitude of the reactances in combination with their losses determines a high frequency current intensity in the plasma segment that is suitable for medical applications.

3. High-frequency device to generate a plasma arc according to claim 1 wherein the first reactance element of the resonant circuit, from which the voltage to generate the plasma arc is derived, is formed by the capacitance of at least one capacitor and the capacitance existing between the electrode lead and the electrode on one hand, and on the other hand the tissue connected to the resonant circuit by way of an earth electrode as well as a lead that connects the resonant circuit to this earth electrode.

4. High-frequency device to generate a plasma arc according to claim 1 wherein the high-frequency generator has a predetermined intrinsic frequency.

5. High-frequency device to generate a plasma arc according to claim 1 wherein the human tissue is connected to a connection of the high-frequency generator that is at the earth potential, the first reactance element of the resonant circuit is formed by a circuit in which a capacitor is disposed in parallel with the lead to which the electrode is corrected and a common effective capacitance formed by the lead and the electrode together with the parallel capacitor forms a reactance with a negative value equal to that of the second reactance element implemented as a series inductor.

6. High-frequency device to generate a plasma arc according to claim 5 wherein the second reactance element is implemented as an inductive reactance element consisting of an inductor and a capacitor disposed in parallel, and the common effective capacitance formed by the lead and electrode together with the capacitor forms a reactance with a negative value equal to that of the second reactance element implemented by the parallel arrangement of the inductor and capacitor.

7. High-frequency device to generate a plasma arc according to claim 2 wherein the first reactance element of the resonant circuit is formed by the arrangement of an inductor in parallel with the lead to which the electrode is attached, and the common effective capacitance formed by the lead and electrode together with the inductor forms a reactance with a negative value equal to that of the second reactance element implemented as a series capacitor.

8. High-frequency device to generate a plasma arc according to claim 7 wherein the tissue is connected, by way of an earth electrode in contact with the patient to the connector of the high-frequency generator that is at the earth potential.

9. High frequency device to generate a plasma arc according to claim 1 wherein the electrode lead to the patient and to the electrode at the operation site is constructed as an insulated unipolar conductor.

10. High-frequency device to generate a plasma arc according to claim 8 wherein the electrode lead to the patient and to the electrode at the operation site is constructed as the internal conductor in a coaxial cable with coaxial shielding conductor having an external insulation layer that protects against contact with the tissue, and the coaxial shielding conductor is connected to the earth electrode in contact with the patient.

11. High-frequency device to generate a plasma arc according to claim 1 wherein the electrode lead to the patient and to the electrode at the operation site is constructed as the internal conductor in a coaxial cable with coaxial shielding conductor having an external insulation layer that protects against contact with the tissue, and the coaxial shielding conductor at its one end is connected to the connector of the high-frequency generator that is at the earth potential and at its other end, in the immediate vicinity of the operation site, comprises an earth electrode, which is in electrically conducting contact with the shielding conductor and which by making contact with an area of the tissue can be electrically connected thereto.

12. High-frequency device to generate a plasma arc according to claim 1 wherein to achieve a high spatial selectivity of the plasma arc a stream of noble gas, preferably a stream of argon gas, with low ionization field strength is directed onto the tissue to be treated, such that the noble as is guided to the operation site in the internal conductor, within the coaxial shielding conductor or in a tube parallel to the latter.

13. High-frequency device to generate a plasma arc according to claim 6 wherein in order to select various current intensities in the plasma arc, the second reactance element implemented as capacitance is suitably selected from a first group of capacitors by means of a first switch and to fulfill the resonance condition the parallel inductor and the effective capacitor of the lead with attached electrode are connected in parallel with a suitable capacitor, which is selected from a second group of capacitors by means of a second switch.

14. High-frequency device to generate a plasma arc according to claim 5 wherein in order to select various current intensities in the plasma arc, the second reactance element implemented as a series inductor is suitably selected from a first group of inductors by means of a first switch and to fulfill the resonance condition the effective capacitor of the lead with attached electrode is connected in parallel with a suitable capacitor, which is selected from a group of capacitors by means of a second switch.

15. High-frequency device to generate a plasma arc according to claim 1 wherein to a high-frequency generator, which is also designed for other applications, there is connected a transformer with several selectable settings of the voltage ratio, and connected thereto is a first switch with which to preselect the voltage ratio.

16. High-frequency device to generate a plasma arc according to claim 1 further comprising a high-impedance HF-current source and a resonance transformation circuit that converts the high-impedance HF-current source into a high-frequency voltage source with low-impedance internal resistor.

17. High-frequency device to generate a plasma arc according to claim 1 wherein the high-frequency generator is formed by a high-frequency voltage source with periodic signal waveform, preferably a square wave, and with low internal resistance, which in particular is of the order of magnitude of the characteristic impedances of coaxial cables.

18. High-frequency device to generate a plasma arc according to claim 17 wherein the high-frequency generator with square-wave signal is formed by a DC voltage source with a complementary circuit in parallel therewith made of switching transistors operated push-pull mode and the latter are triggered by a pulse generator, which by means of a current decoupler is synchronized for measurement or the resonant-circuit current, and the output voltage of the high-frequency generator thus formed is applied to the common source electrode of the switching transistors.

19. High-frequency device to generate a plasma arc according to claim 1 wherein the high-frequency generator has a predetermined intrinsic frequency and a regulating device is present by means of which the resonance in the resonant circuit can be regulated by adjustment of at least one of the two reactance elements.

20. High-frequency device to generate a plasma arc according to claim 19 wherein the resonance in the resonant circuit produced by adjusting the first reactance element is determined by the following: a current decoupler is present in the circuitry of the resonant circuit and the decoupled current is sent to an amplitude indicator where it is evaluated, and downstream of the amplitude indicator in the circuit a regulator for adjustment of the reactance element is disposed, in which the signal from the amplitude indicator is evaluated in such a way that the resonant current and hence the voltage at the first reactance element is set to a maximum.

21. High-frequency device to generate a plasma arc according to claim 19 wherein the regulating device comprises a set-point transmitter for presetting the current in the plasma arc and hence the patient current.

22. High-frequency device to generate a plasma arc according to claim 21 wherein a patient-current decoupler, a patient-current indicator and a patient-current regulator are provided and the current in the plasma arc can be regulated by setting the second reactance element and the high-frequency voltage source to the value prescribed by the set-point transmitter.

23. High-frequency device to generate a plasma arc according to claim 1 wherein at least one of the two reactance elements is formed entirely or in part by a variable inductor, the inductance of which is determined in an inertia-free manner by premagnetization of a ferrite core with variable permeability, wherein the premagnetization is adjusted by means of a premagnetization winding through which a premagnetization current flows.

24. High-frequency device to generate a plasma arc according to claim 23 wherein the variable premagnetization current is adjusted by means of a controlled variable DC voltage source.

25. High-frequency device to generate a plasma arc according to claim 1 wherein the high-frequency voltage source and at least parts of the resonant circuit, in particular together with regulating or adjustment devices for adjusting the resonant frequency or for adjusting the intensity of the plasma current, are disposed in a housing that ensures the patient's safety, to which is connected the lead with attached electrode.

* * * * *

UNITED STATES PATENT AND TRADEMARK OFFICE
CERTIFICATE OF CORRECTION

PATENT NO. : 6,565,558 B1
DATED : May 20, 2003
INVENTOR(S) : Lindenmeier et al.

It is certified that error appears in the above-identified patent and that said Letters Patent is hereby corrected as shown below:

<u>Title page,</u>
Item [76], Inventors, "Forstenriederstrasse" should read -- Fürstenriederstrasse --

Signed and Sealed this

Twenty-third Day of March, 2004

JON W. DUDAS
*Acting Director of the United States Patent and Trademark Office*